United States Patent
Arai et al.

[11] Patent Number: 5,941,704
[45] Date of Patent: Aug. 24, 1999

[54] CROWN CAGE FOR BALL BEARING AND DENTAL HAND PIECE INCLUDING THE SAME

[75] Inventors: Hirokazu Arai, Yamatokoriyama; Atsushi Yao, Kashihara, both of Japan

[73] Assignee: Koyo Seiko Co., Ltd., Osaka, Japan

[21] Appl. No.: 09/110,432

[22] Filed: Jul. 6, 1998

Related U.S. Application Data

[63] Continuation-in-part of application No. 08/603,160, Feb. 20, 1996, abandoned.

[30] Foreign Application Priority Data

Feb. 20, 1995 [JP] Japan .................................. 7-031017
Feb. 2, 1996 [JP] Japan .................................. 8-017770

[51] Int. Cl.$^6$ .................................................. F16C 33/44
[52] U.S. Cl. .............................................. 433/114; 384/523
[58] Field of Search ........................... 433/114, 117, 433/132; 384/523, 527; 29/898.067, 898.09

[56] References Cited

U.S. PATENT DOCUMENTS

| | | |
|---|---|---|
| 1,650,853 | 11/1927 | Rouanet . |
| 3,918,778 | 11/1975 | Jacobson et al. . |
| 4,322,879 | 4/1982 | Warchol . |
| 5,199,799 | 4/1993 | Masuda et al. . |
| 5,575,570 | 11/1996 | Uchiyama et al. . |

FOREIGN PATENT DOCUMENTS

| | | |
|---|---|---|
| 139 284 | 12/1979 | Germany . |
| 6-165790 | 6/1994 | Japan . |

*Primary Examiner*—Ralph A. Lewis
*Attorney, Agent, or Firm*—Thelen Reid & Priest LLP

[57] ABSTRACT

A crown cage is applied to a ball bearing for high-speed rotation for a dental hand piece or the like. The cage has a cylinder formed by injection molding of a thermoplastic resin, and pockets for holding balls that are formed at a predetermined circumferential pitch in the cylinder. A first recess including a gate cutting trace at the time of molding, and second recesses for correcting rotational imbalance of the cylinder caused by the first recess, are formed in the cylinder. The recesses have almost the same shape, and are arranged at a predetermined circumferential pitch.

9 Claims, 7 Drawing Sheets

CROWN CAGE FOR BALL BEARING AND DENTAL HAND PIECE INCLUDING THE SAME

CROSS REFERENCE TO RELATED APPLICATION

This application claims priority benefits under 35 U.S.C. § 119 to Japanese Patent Application Serial No. 7-31017 and Japanese Patent Application Serial No. 8-017770.

This application is also a continuation-in-part (CIP) patent application of U.S. application Ser. No. 08/603,160, filed Feb. 20, 1996, and now abandoned.

Both of these documents are incorporated herein by reference.

BACKGROUND OF THE INVENTION

1. Field of the Invention

The present invention relates to a crown cage applied to a ball bearing for high-speed rotation and a dental hand piece including the same.

2. Related Art

In the above-mentioned dental hand piece, a rotating shaft having a grindstone attached to its end is reversibly rotated at high speeds (for example, 300,000 to 400,000 rpm) and the peripheral speed of the grindstone is increased to improve the cutting quality thereof in order to complete teeth cutting work in a short time to reduce an unpleasant feeling of a patient.

When a deep groove ball bearing is employed as a bearing for the dental hand piece or the like, a crown cage is used. As the crown cage, a crown cage having a pocket and the like formed therein by cutting processing using a cylinder made of a thermosetting resin having heat resistance as a material in order to resist sterilization work under high temperatures (for example, 135° C.) within an autoclave has been conventionally put to practical use (see, for example, Japanese Unexamined Patent Publication No. 165790/1994).

In the conventional crown cage, however, cutting processing is required, whereby the number of processes is increased, and the manufacturing cost is increased.

In order to cope with the above-mentioned situation, it is considered that a crown cage for a ball bearing is manufactured by injection molding using a thermoplastic resin.

In order to prevent a gate cutting trace remaining on the surface of the crown cage which is composed of moldings from being projected from the surface of the crown cage, the shape of the crown cage is such a shape that recesses are provided in positions corresponding to a gate position (an area including the gate position). On the other hand, as a metal mold for injection molding, a metal mold having one gate is generally employed, whereby the number of recesses is one.

If the number of recesses is thus only one, the weight balance of the crown cage is worsened. As a result, the occurrence of new problems is expected. For example, the crown cage chatters at the time of high-speed rotation.

SUMMARY OF THE INVENTION

The present invention has been made in view of the above-mentioned technical background and has for its object to provide a crown cage for a ball bearing having a good weight balance and a dental hand piece including the same by injection molding using a thermoplastic resin.

In order to attain the above-mentioned object, in a crown cage for a ball bearing which is composed of injection moldings of a thermoplastic resin, a crown cage for a ball bearing in one mode of the present invention is characterized by comprising a cylinder having a gate position at the time of injection molding set on its end surface or its peripheral surface, a plurality of pockets for holding balls which are formed at a predetermined circumferential pitch on one end surface ofthe cylinder, a first recess formed in the cylinder and including the gate position, and a second recess formed in the cylinder for correcting an unbalance on rotation of the cylinder by the first recess.

When only the first recess for preventing a gate cutting trace from being projected is provided, a cage causes an unbalance on rotation. In the mode, however, the unbalance can be corrected by the second recess. The weight balance during rotation of the crown cage obtained by the injection molding using the thermoplastic resin is improved. As a result, the crown cage does not chatter at the time of high-speed rotation.

If the above-mentioned thermoplastic resin is a thermoplastic polyimide resin to which 5 to 10% by weight of polytetrafluoroethylene and 10 to 20% by weight of graphite are added, it is suitable for use as a crown cage for a ball bearing for a dental hand piece in that the abrasion resistance thereof can be improved.

Liquid paraffin series lubricating oil (corresponding to ISO VG68, for example) is used for the ball bearing for the dental hand piece. However, the lubricating oil may be supplied not more than one or two times per month in many cases. Consequently, the ball bearing is employed in rotation at very high speeds (for example, 400,000 rpm) in an almost non-lubricant state. Even if the ball bearing is employed under such severe conditions, the cage can exhibit sufficient abrasion resistance, provided that it is made of a thermoplastic polyimide resin to which the polytetrafluoroethylene and the graphite are added at the foregoing mixture ratio. Further, the cage can resist sterilization work under high temperatures using an autoclave or a chemiclave. The cage is also suitable for the application to the dental hand piece from this point.

The foregoing and other objects, features, aspects and advantages of the present invention will become more apparent from the following detailed description of the present invention when taken in conjunction with the accompanying drawings.

DETAILED DESCRIPTION OF THE PREFERRED EMBODIMENTS

Embodiments of the present invention Will be described in detail on the basis of attached drawings.

Figure 6:
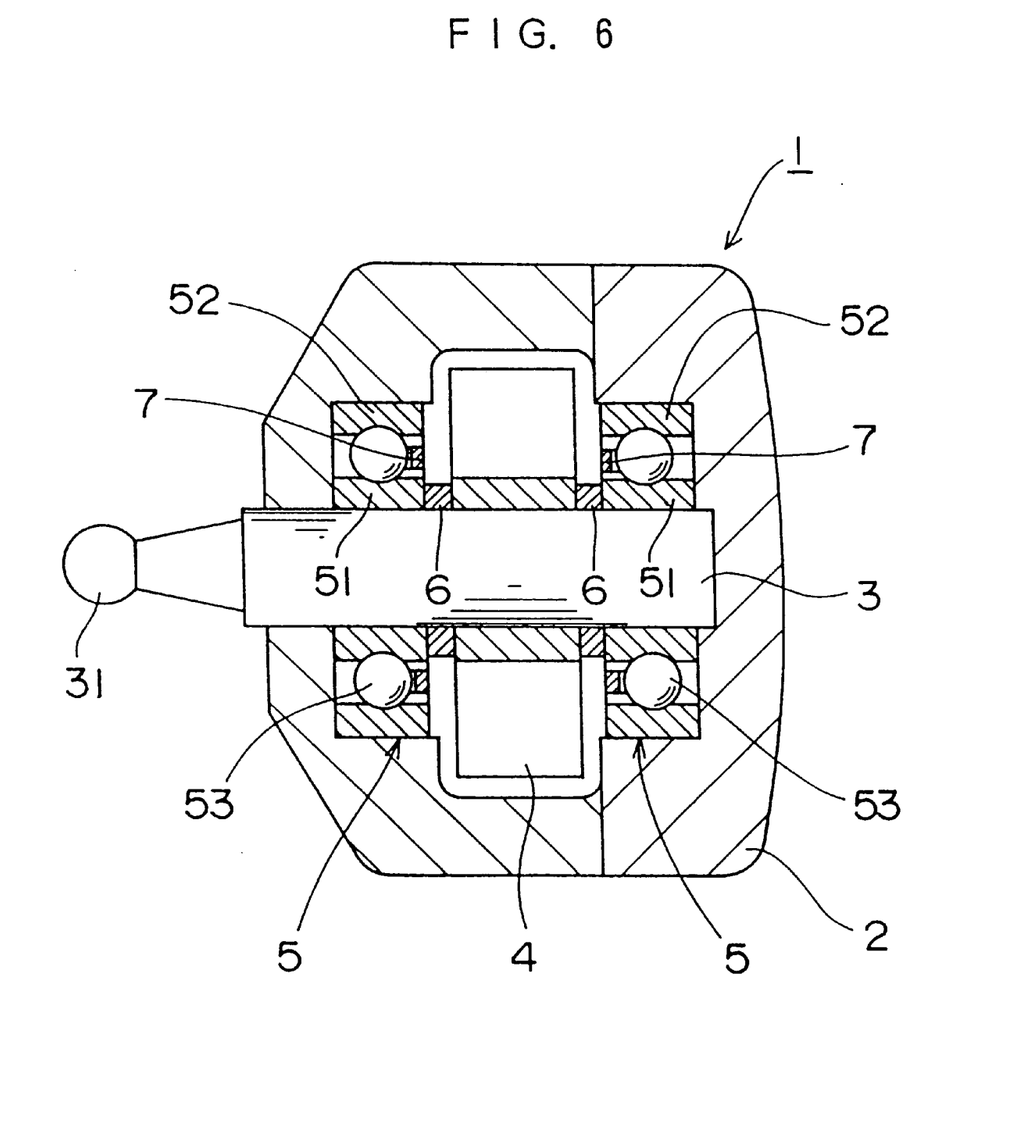
FIG. 6 is a cross-sectional view showing the construction of a dental hand piece to which the crown cage is applied.

Referring to FIG. 6 showing a dental hand piece including a crown cage for a ball bearing according to one embodiment of the present invention, a dental hand piece 1 comprises (1) a housing 2, (2) a rotating shaft 3 arranged in the housing 2 with its one end projected outward, (3) a turbine blade 4 fixed to a portion in the housing 2 of the rotating shaft 3, and (4) a deep groove ball bearing 5 attached to the housing 2 for rotatably supporting the rotating shaft 3 on both sides of the turbine blade 4. In the dental hand piece 1, compressed air is supplied to the housing 2, whereby the turbine blade 4 and the rotating shaft 3 are rotated at high speeds. At this time, the air passes through the inside of the ball bearing 5, to exhibit the cooling effect.

A dental burr 31 is formed in an end of the rotating shaft 3 projected outward from the housing 2, and a hand with a grindstone (not shown) is connected to the dental burr 31.

A spacer 6 for binding the axial movement of the turbine blade 4 is interposed between the turbine blade 4 and the ball bearing 5.

The ball bearing 5 comprises an inner ring 51, an outer ring 52, and a plurality of balls 53 rolling between the inner ring 51 and the outer ring 52. The inner ring 51 and the outer ring 52 are made of a metal having high corrosion resistance such as stainless steel (JIS SUS440C, for example). The ball 53 is made of ceramics mainly composed of silicon nitride or SIALON, and is held by a crown cage 7 which is incorporated into the ball bearing 5.

Figure 1:
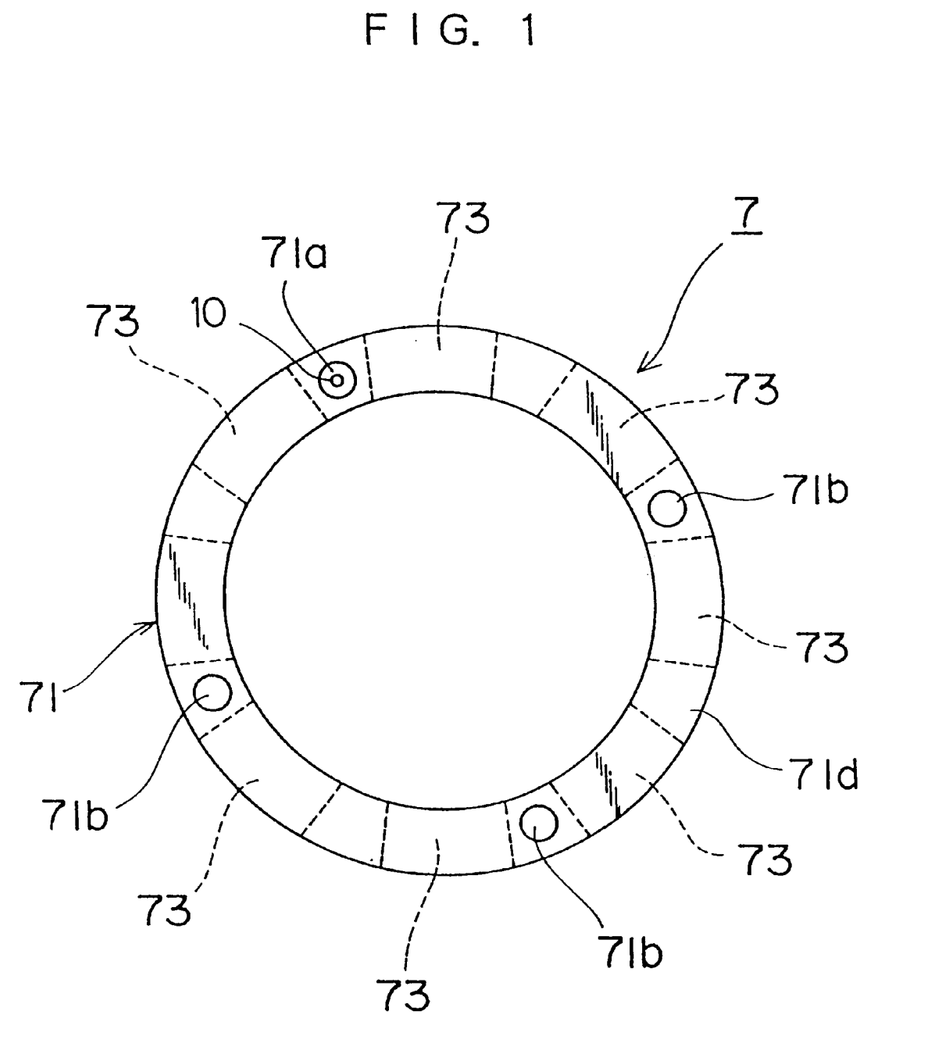
FIG. 1 is a bottom view showing a crown cage for a ball bearing according to one embodiment of the present invention.
Figure 3:
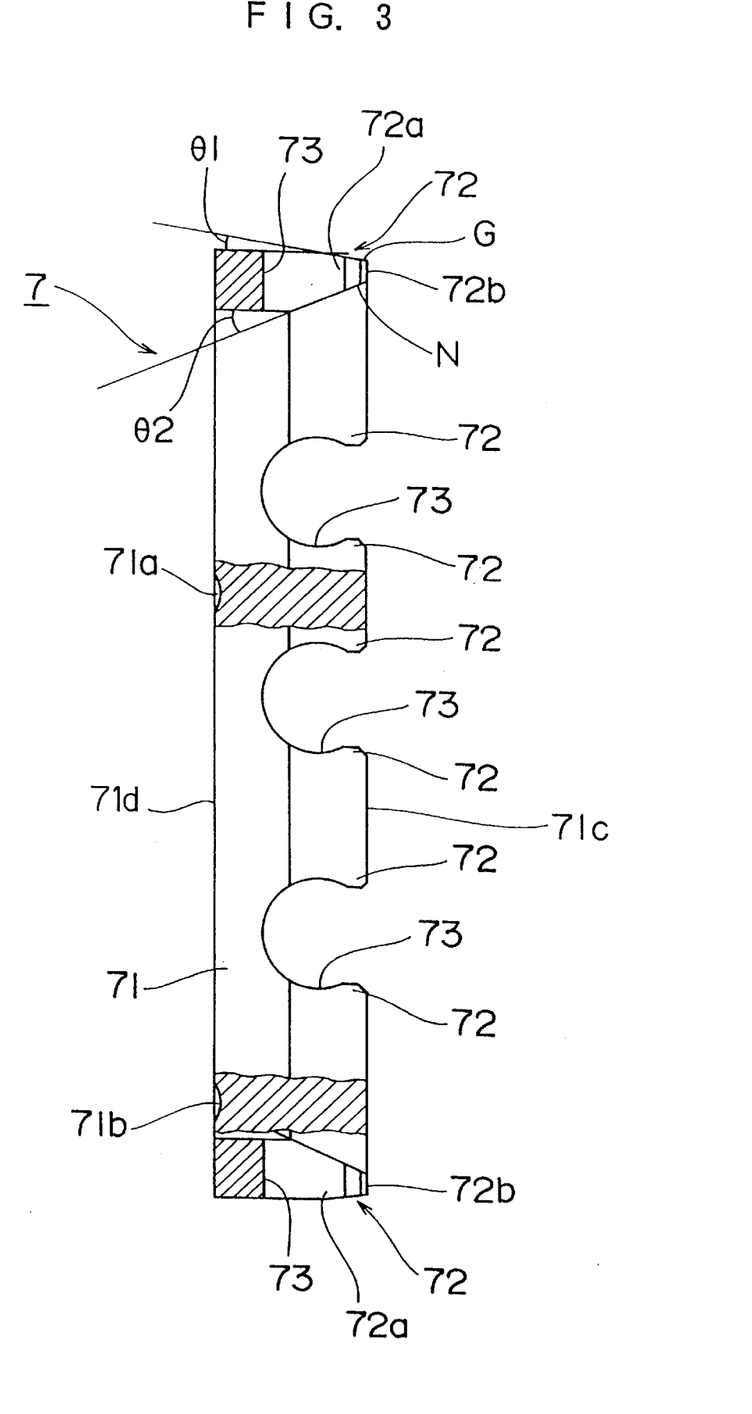
FIG. 3 is an enlarged cross-sectional view showing the crown cage.

Referring to FIGS. 1 and 3, the crown cage 7 according to the present embodiment is manufactured by injection molding using a thermoplastic resin having heat resistance, and comprises (1) a cylinder 71, and (2) pockets 73 provided at a predetermined circumferential pitch on one end surface 71c of the cylinder 71 and each having a pair of claws 72 formed therein so as to hold a ball 53. The resin does not include a reinforced fiber such as a glass fiber. This is for avoiding the possibility that an exposed fiber wears away and is tangled in a track surface on a pocket surface.

As in the present embodiment, in the crown cage for a ball bearing 7 for the dental hand piece, it is preferable to use a thermoplastic polyimide resin (hereinafter referred to as thermoplastic TPI) to which polytetrafluoroethylene (hereinafter simply referred to as PTFE) is added in amount of 5 to 10% by weight and to which graphite is added in amount of 10 to 20% by weight.

The reason for this is that the dental hand piece has been subjected to sterilization work under high temperatures within an autoclave or a chemiclave in recent years, and the above-mentioned crown cage made of the thermoplastic TPI can resist the sterilization work. The cage for a ball bearing for the dental hand piece is very small in size. Consequently, it is required that a resin for molding the cage is superior in flowability at the time of molding. As a resin for molding the cage, it is required that a mold release can be formed by forcibly pulling moldings out of a metal mold in a portion of the pocket holding the ball in the cage. On the other hand, the thermoplastic TPI can satisfy requirements relating to such flowability and mold release characteristics (generically named molding characteristics).

Liquid paraffin series lubricating oil (corresponding to ISO VG68, for example) is used for the ball bearing for the dental hand piece. However, the lubricating oil may be supplied not more than one or two times per month in many cases. Consequently, the ball bearing is employed in rotation at very high speeds (for example, 400,000 rpm) in an almost non-lubricant state. Even if the ball bearing is employed under such severe conditions, the cage can exhibit sufficient abrasion resistance, provided that it is made of a thermoplastic polyimide resin to which the PTFE and the graphite are added at the foregoing mixture ratio.

The foregoing mixture ratio of the PTFE and the graphite is preferable because a mixture ratio of the PTFE of less than 5% by weight in all the ingredients of the crown cage 7 results in an excessive abrasion of cage 7, and the mixture ratio of PTFE of more than 10% by weight results in a low strength of cage 7, while a mixture ratio of graphite of less than 10% by weight in all the ingredients of the crown cage 7 results in an unstable friction between cage 7 and the balls 53, and the mixture ratio of graphite of more than 20% by weight results in a low strength of cage 7. When only 5 to 10% by weight of PTFE is added and no graphite is added, the abrasion is unstable, which is not preferable. In addition, when only 10 to 20% by weight of graphite is added and no PTFE is added, the is excessive, which is not preferable.

On the other hand, examples of a resin having heat resistance other than the TPI include polyphenylene sulfide (hereinafter referred to as PPS), polyether sulfide (hereinafter referred to as PES), polyether nytril (hereinafter referred to as PEN), and polyether ether ketone (hereinafter referred to as PEEK). The resins are suitable for use in cages employed for ball bearings other than the ball bearing for the dental hand piece. Specifically, the PES is liable to melt in methyl chrome, whereby the PES can be applied to cages employed in an environment having no methyl chrome. Since the PEN is inferior in flowability, and small-sized products of the PEN are difficult to manufacture, the PEN is suitable for cages of a certain degree of size or more. The PEEK is hard and has no flexibility. Although the PEEK cannot be applied to cages which are rotated at very high speeds (300,000 rpm), for example, the cage for the dental hand piece, therefore, it can be applied to cages which are not rotated at very high speeds.

Figure 4:
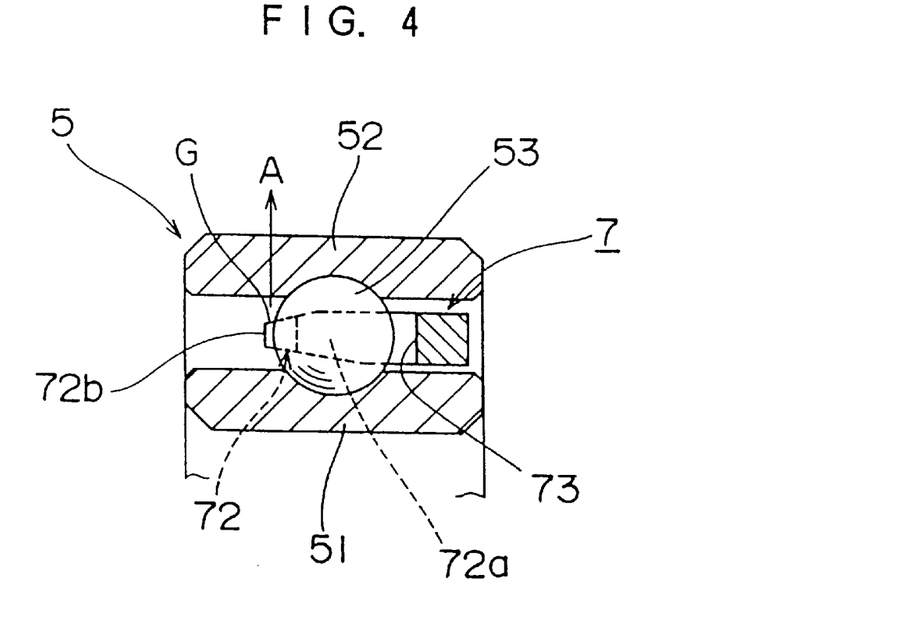
FIG. 4 is a cross-sectional view showing a principal part of the ball bearing into which the crown cage is incorporated.

As clearly shown in FIG. 3, an end 72a on the side of an opening of the pocket of the claw 72 is so formed as to be thinner than an end on the side of the cylinder 71 by successively inclining its outside diameter surface G and its inside diameter surface N toward an end surface 72b on the side of the opening of the pocket of the claw 72. An angle of inclination θ1 of the outside diameter surface G is set approximately at 10°, for example, and an angle of inclination θ2 of the inside diameter surface N is set approximately at 15°, for example. The reason why the end 72a on the side of the opening of the pocket of the claw 72 is thus so formed as to be thinner than the end on the side of the cylinder 71 is that the claw 72 is made lightweight, and a centrifugal force exerted on the claw 72 is reduced at the time of high-speed rotation, to restrain expansion of the claw 72 toward the outer ring 52 (in a direction indicated by an arrow A), as shown in FIG. 4. Particularly, the outside diameter surface G of the end 72a on the side of the opening of the pocket of the claw 72 is inclined for the purpose of preventing the outside diameter surface G from being brought into contact with the inside diameter of the outer ring 52 when the claw 72 expands toward the outer ring 52 (in the direction indicated by the arrow A).

As clearly shown in FIG. 1, a first recess 71a corresponding to a gate position at the time of molding and a plurality of (three in FIG. 1) second recesses 71b for correcting a rotational imbalance caused by the first recess 71a are formed on the other end surface 71d of the cylinder 71. A gate cutting trace 10, which is to be hereafter described, exists in a substantially central position of the first recess 71a.

The gate cutting trace 10 does not exist in any of the second recesses 71b. In terms of elimination of the gate cutting trace 10, the forms of the first and second recesses 71a and 71b are substantially the same.

The first and second recesses 71a and 71b are arranged at a predetermined circumferential pitch. Further, each of the recesses 71a and 71b is arranged in an intermediate position between the adjacent pockets 73.

Figure 2:
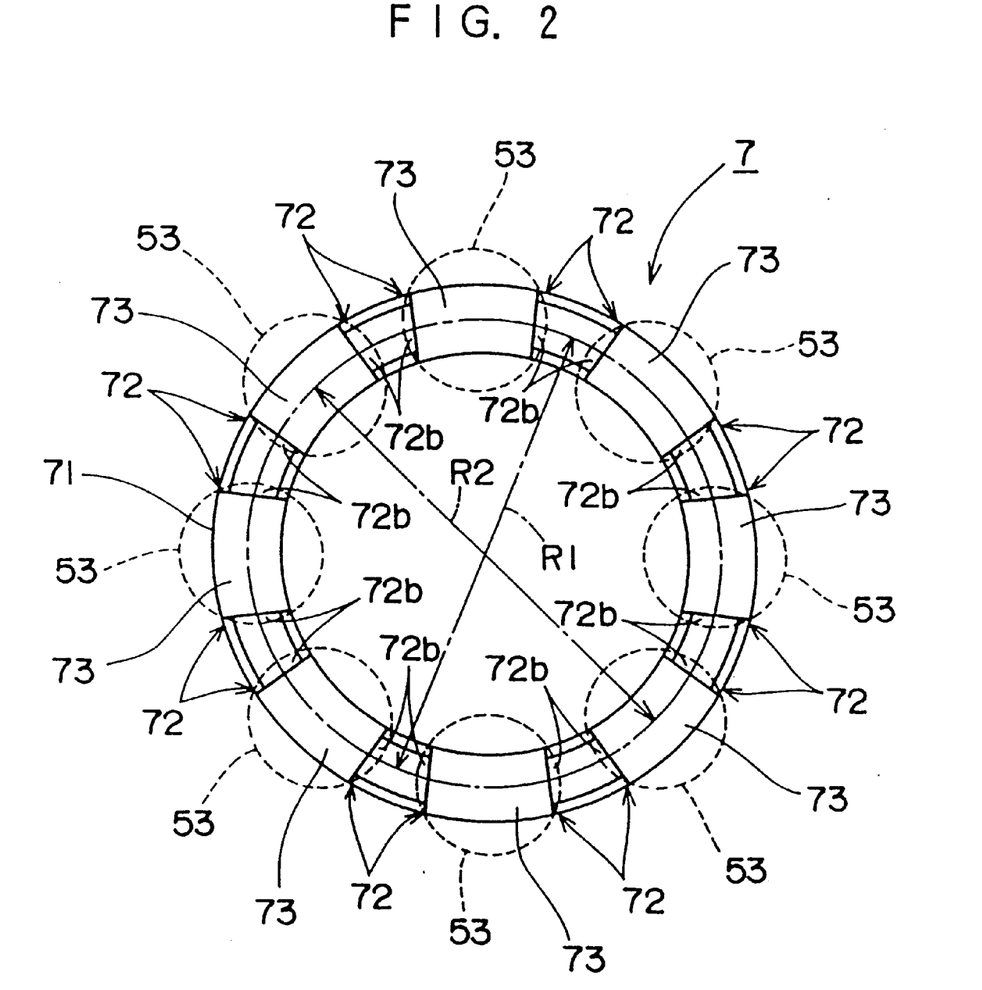
FIG. 2 is a top view showing the crown cage.

As clearly shown in FIG. 2, the diameter R1 of a circle C1 connecting the centers of the wall thicknesses of the end surfaces 72b on the side of the openings of the pockets of the respective claws 72 almost coincides with the diameter R2 of the circle C2 connecting the centers of the balls 53 held in the respective pockets 73. The diameter R1 of the circle C1 is a PCD (pitch circle diameter) of the end surface 72b on the side of the openings of the pockets of the claws 72, and the diameter R2 of the circle C2 is a PCD of the balls 53 held in the pockets 73.

Figure 8A:
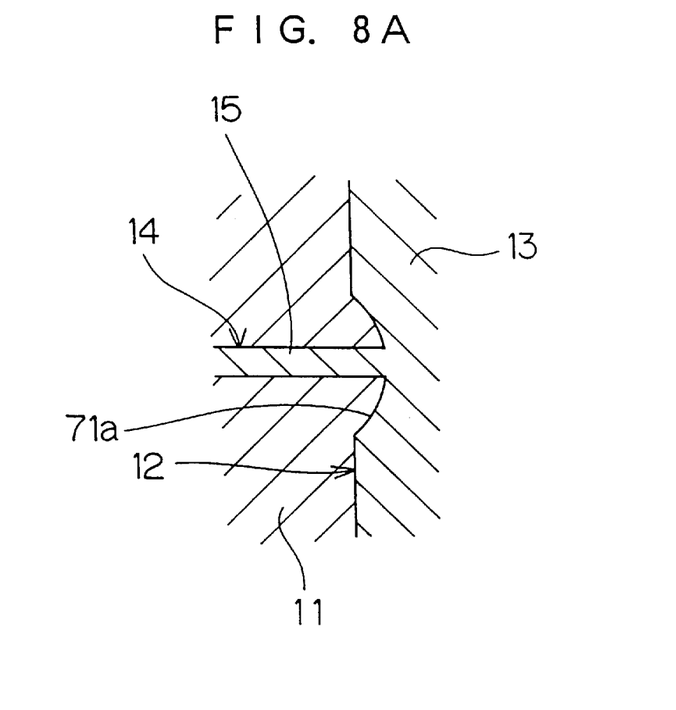
FIG. 8A is a schematic cross-sectional view showing a forming mold and a molded product.
Figure 8B:
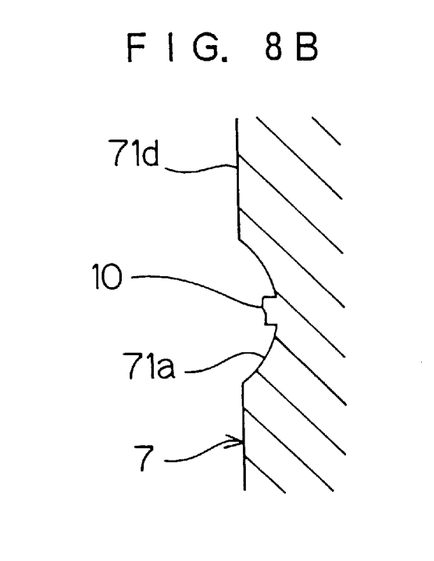
FIGS. 8B and 8C are schematic cross-sectional views showing the molded product detached from the forming mold.

Explanation for the existence of the gate cutting trace 10 in the first recess 71a is given as follows, with reference to FIGS. 8A and 8B. That is, a first part 13 that is the main body of the cage 7, and a second part 15 that is formed in the gate 14 and has the same form as the gate 14, are included in the molded resin 12 upon completion of molding in the forming mold 11, as shown in FIG. 8A. The first and second members 13 and 15 are integrally connected.

Figure 8C:
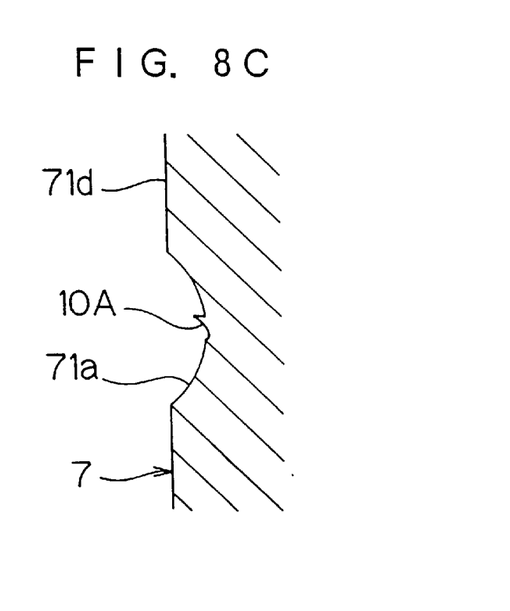

After that, when the first part 13 (as the cage 7) is detached from the forming mold 11, the second part 15 is cut off at the gate. Consequently, as shown in FIG. 8B, the cut surface of the second part 15 is traced as the cutting trace 10 without fail on the inner surface of the first recess 71a in the cage 7 which is the final structure of the molding. Further, at least one part of the cut surface composing a gate cutting trace 10A may be more depressed than the first recess 71a, as shown in FIG. 8C.

If the above-mentioned crown cage 7 is rotated at high speeds, for example, 400,000 rpm in a case where it has only the first recess 71a including a gate cutting trace 10, the cage 7 causes unbalanced deflection due to the first recess 71a. On the other hand, in the present invention, an unbalance on rotation which is caused by the first recess 71a is corrected by the second recesses 71b, whereby a balance on rotation can be improved. Specifically, dummy second recesses 71b having the same shape as that of the first recess 71a are provided, and the recesses 71a and 71b are arranged at a predetermined circumferential pitch on the other end surface 71d of the cylinder 71, whereby the weight balance during the rotation of the crown cage 7 obtained by injection molding using a thermoplastic resin is improved. As a result, the crown cage 7 does not chatter in a centrifugal direction at the time of high-speed rotation. The projection (a residual stub formed as a result of injection molding) and/or recess are minute, and therefore, the gate cutting trace 10 hardly affects the rotational balance.

Figure 5:
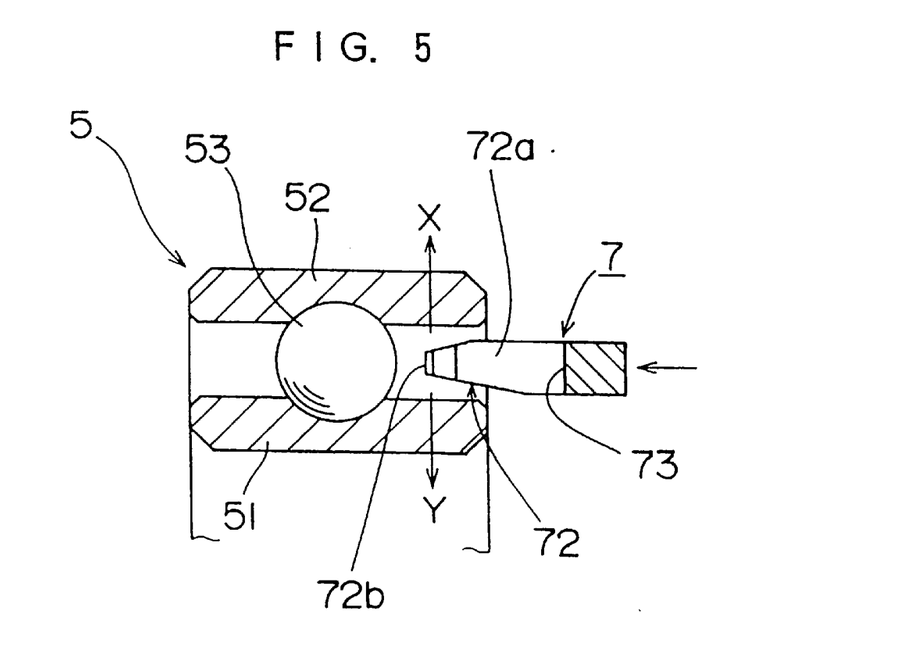
FIG. 5 is a cross-sectional view showing a principal part of the ball bearing into which the crown cage is to be inserted.

The diameter R1 of the circle C1 connecting the centers of the wall thicknesses of the end surfaces 72b on the side of the openings of the pockets of the respective claws 72 and the diameter R2 of the circle C2 connecting the centers of the balls 53 held in the respective pockets 73 almost coincide with each other. In inserting the crown cage 7 into the ball bearing 5 as shown in FIG. 5, therefore, the end surface 72b on the side of the opening of the pocket of the claw 72 abuts against the ball 53, whereby no bending forces toward the outer ring 52 (in a direction indicated by an arrow X) and toward the inner ring 51 (in a direction indicated by an arrow Y) are not exerted on the crown cage 7. Therefore, the end surface 72b on the side of the opening of the pocket of the claw 72 which abuts against the ball 53 does not escape toward the outside diameter or the inside diameter of the ball 53, whereby the ball 53 can be smoothly contained in the pocket 73. As a result, it is possible to smoothly perform work for inserting the crown cage 7 into the ball bearing 5.

The present invention is not limited to the above-mentioned embodiment. For example, although in the above-mentioned embodiment, the outside diameter surface G and the inside diameter surface N of the end 72a on the side of the opening of the pocket of the claw 72 are inclined to make the end 72a on the side of the opening of the pocket of the claw 72 thinner than the end on the side of the cylinder 71, only either one of the outside diameter surface G and the inside diameter surface N of the end 72a on the side of the opening of the pocket of the claw 72 may be inclined.

Although in the above-mentioned embodiment, the first and second recesses 71a and 71b are formed at a predetermined circumferential pitch on the other end surface 71d of the cylinder 71, the recesses 71a and 71b may be formed at a predetermined circumferential pitch on the inner peripheral surface or the outer peripheral surface of the cylinder 71. In either case, the position where the first recess 71a is provided is decided by the gate position, and the second recesses 71b are decided by the first recess 71a. Specifically, when the gate position is provided on the other end surface 71d of the cylinder 71, it is preferable that both the recesses 71a and 71b are also provided on the other end surface 71d of the cylinder 71. On the other hand, when the gate position is provided on the inner peripheral surface (or the outer peripheral surface) of the cylinder 71, it is preferable that both the recesses 71a and 71b are also provided on the inner peripheral surface (or the outer peripheral surface) of the cylinder 71. The first recess 71a and the second recesses 71b may be respectively arranged on the other end surface 71d and the peripheral surface of the cylinder 71, or vice versa, provided that the balance on rotation of the cage 7 is ensured. Further, the sizes of both the recesses 71a and 71b may differ, provided that the balance on rotation of the cage 7 is ensured.

Although in the above-mentioned embodiment, description was made of an example in which the crown cage 7 is applied to the ball bearing for the dental hand piece, it may be applied to a ball bearing for high-speed rotation for a machine tool or the like.

It goes without saying that various design changes and corrections can be made within the range of the claims of the present invention.

Test. A crown cage for a ball bearing for a dental hand piece which has the same shape as that shown in FIG. 1 is formed by injection molding of thermoplastic TPI, to prepare test examples 1 and 2 and comparative examples 1 to 5 in which the contents of PTFE and graphite are changed into various values as shown in Table 1.

TABLE 1

|  | mixture ratio (% by weight) | | | results of test | |
|---|---|---|---|---|---|
|  | TPI | PTFE | graphite | degradation of strength | durability test |
| test example 1 | 85 | 5 | 10 | ○ | ○ |
| test example 2 | 70 | 10 | 20 | ○ | ○ |
| comparative example 1 | 82 | 3 | 15 | ○ | X: abrasion increase |
| comparative example 2 | 70 | 15 | 15 | X: degradation increase | ○ |
| comparative example 3 | 87 | 8 | 5 | ○ | X: friction is unstable |
| comparative example 4 | 67 | 8 | 25 | X: degradation increases | ○ |

○ is good, X is poor

Tests were carried out under the following conditions using cages in the respective examples, to obtain the results shown in Table 1.

Test Conditions. Determination of initial values of breaking strengths of cages H are made in each example with both of the jigs 8 and 9 attached to the protruding portions 81 and 91 are being pulled upwards and downwards respectively as indicated by the arrows in FIGS. 7A and 7B.

Figure 7A:
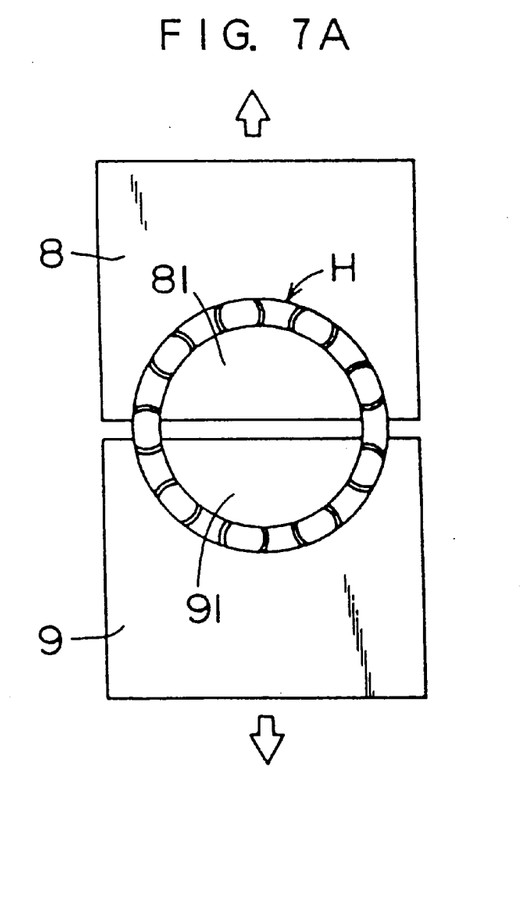
FIG. 7A is a schematic front view showing an equipment for finding the breaking strength of the crown cage.
Figure 7B:
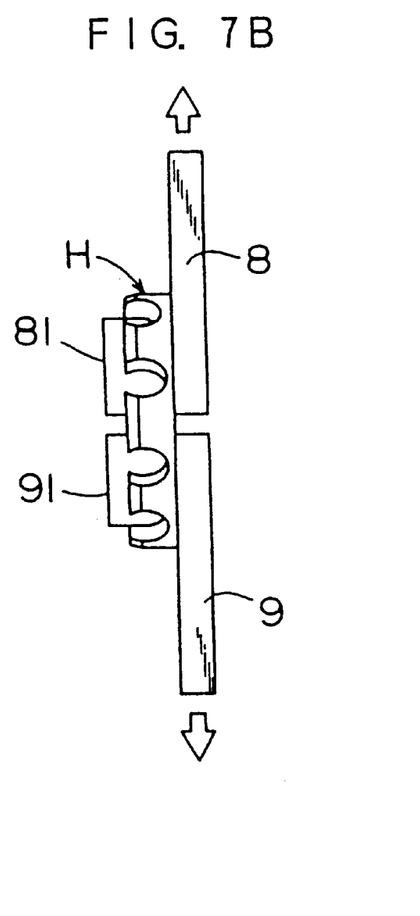
FIG. 7B is a schematic side view showing the equipment.

The process of leaving the cages for five minutes under high-pressure stream at a temperature of 135° C. within an autoclave, then leaving the cages for ten minutes under dry air at a temperature of 180° C. and drying the cages is taken as one cycle, and is repeated in 500 cycles, to examine degradation of the strength of the cages in each example. Breaking strengths of the cages which are taken out of the autoclave are determined using the jigs 8 and 9 in each example, and then the breaking strengths of the cages taken out of the autoclave are compared to the initial values of breaking strengths of the cages H to find degrees of degradations in strengths.

Further, degrees of abrasion of cages which are inserted into ball bearings are examined in each example after a durability test under a predetermined condition (a condition of 300 hours of operating time in which a process of 15 seconds of operation under 120 gf of load and 15 seconds of no operation is repeated with oil supply of every 30 minutes). Rotation torque is also examined before and after the durability test to find the change in the rotation torque before and after the durability test. If the change in the rotation torque is great, the coefficient friction becomes greater and the friction becomes more unstable.

Results of Test. The results of the test in the test examples 1 and 2 prove that the crown cage made of thermoplastic TPI to which 5 to 10% by weight of PTFE and 10 to 20% by weight of graphite are added are not easily affected by the autoclave and has superior durability.

On the other hand, the results of the test in the comparative example 1 prove that if the content of PTFE is less than 5% by weight, the abrasion increases even if the content of graphite is in the preferable range, whereby the crown cage is not superior in durability.

The results of the test in the comparative example 2 prove that if the content of PTFE exceeds 10% by weight, the strength becomes lower even if the content of graphite is in the preferable range, whereby the crown cage is not superior in durability.

The results of the test in the comparative example 3 prove that if the content of graphite is less than 10% by weight, the friction becomes unstable even if the content of PTFE is in the preferable range, whereby the crown cage is not superior in durability.

The results of the test in the comparative example 4 prove that if the content of graphite exceeds 20% by weight, the strength becomes lower even if the content of PTFE is in the preferable range, whereby the crown cage is not superior in durability.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A ball bearing crown cage made during an injection molding process in which thermoplastic molten resin is injected through a predetermined gate position, the crown cage comprising a cylinder having:

a first end surface;

a second end surface, located axially opposite the first end surface;

at least one peripheral surface joining the first and second end surfaces;

plural pockets, formed in the first end surface at regular angular intervals, for holding balls;

a first recess that has a gate cutting trace formed as a result of the injection molding process; and at least one dummy recess for correcting a rotational imbalance caused by the first recess.

2. The crown cage of claim 1, wherein:

the first recess and the at least one dummy recess have almost the same shape when the gate cutting trace is omitted, and are arranged at regular angular intervals around the cylinder.

3. The crown cage of claim 1, further comprising:

pairs of tapered claws, formed on the first end surface, for holding balls in respective pockets from opposite sides of each pocket.

4. The crown cage of claim 1, further comprising:

pairs of claws, formed on the first end surface, for holding balls in respective pockets from opposite sides of each pocket;

wherein (1) a diameter of a circle constituting a center line of the first end surface and (2) a diameter of a circle connecting centers of the balls held in the pockets, are almost coincident.

5. The crown cage of claim 1, wherein the thermoplastic resin is a thermoplastic polyimide resin to which are added:

5% to 10% by weight of polytetrafluoroethylene; and

10% to 20% by weight of graphite.

6. A dental hand piece comprising:

a) a rotating shaft to which a turbine blade is fixed; and b) a ball bearing for rotatably supporting the rotating shaft, the ball bearing including a crown cage made during an injection molding process in which thermoplastic molten resin is injected through a predetermined gate position;

wherein:

A) the crown cage includes a cylinder having:

1) a first end surface;

2) a second end surface, located axially opposite the first end surface;

3) at least one peripheral surface joining the first and second end surfaces;

4) plural pockets, formed in the first end surface at regular angular intervals, for holding balls;
5) a first recess that has a gate cutting trace formed as a result of the injection molding process; and
6) at least one dummy recess for correcting a rotational imbalance caused by the first recess; and B) the thermoplastic molten resin is a thermoplastic polyimide resin to which are added:
5% to 10% by weight of polytetrafluoroethylene; and
10% to 20% by weight of graphite.

7. The dental hand piece of claim 6, wherein:
the first recess and the at least one dummy recess have almost the same shape when the gate cutting trace is omitted, and are arranged at regular angular intervals around the cylinder.

8. The dental hand piece of claim 6, further comprising:
pairs of tapered claws, formed on the first end surface, for holding balls in respective pockets from opposite sides of each pocket.

9. The dental hand piece of claim 6, further comprising:
pairs of claws, formed on the first end surface, for holding balls in respective pockets from opposite sides of each pocket;
wherein (1) a diameter of a circle constituting a center line of the first end surface and (2) a diameter of a circle connecting centers of the balls held in the pockets, are almost coincident.

\* \* \* \* \*